United States Patent [19]

Lau

[11] 4,374,291

[45] Feb. 15, 1983

[54] SYNTHESIS OF BIS(ETHYNYLPHENYL) COMPOUNDS

[75] Inventor: Kreisler S. Y. Lau, Alhambra, Calif.

[73] Assignee: Hughes Aircraft Company, Culver City, Calif.

[21] Appl. No.: 318,716

[22] Filed: Nov. 6, 1981

[51] Int. Cl.$^3$ ............................................. C07C 15/16
[52] U.S. Cl. .................................... 585/320; 556/465; 564/431; 568/34; 568/58; 568/14; 568/332; 570/129; 570/144; 585/25; 585/469
[58] Field of Search .................... 585/25, 320, 469; 570/129, 144; 568/34, 58, 14, 332; 564/431; 556/465

[56] References Cited

U.S. PATENT DOCUMENTS

| | | | |
|---|---|---|---|
| 4,098,767 | 7/1978 | Bilow | 526/262 |
| 4,120,885 | 10/1978 | Diamond | 568/58 |
| 4,147,729 | 4/1978 | Zupančič et al. | 568/332 |
| 4,284,834 | 8/1981 | Austin et al. | 585/25 |
| 4,296,264 | 10/1981 | Diamond | 570/129 |
| 4,301,313 | 11/1981 | Marshall et al. | 570/129 |

*Primary Examiner*—Curtis R. Davis
*Attorney, Agent, or Firm*—A. W. Karambelas; W. H. MacAllister; W. J. Bethurum

[57] ABSTRACT

Bis(ethynylphenyl) compounds are prepared by an improved synthesis process which increases yield and is suitable for large scale synthesis operations. Aromatic dianilines are diazotized to form aromatic halides that are subsequently coupled with an end-protecting group having acetylenic moieties. The end-protecting groups are subsequently removed leaving the desired diethynyl derivative in quantitative yields.

11 Claims, 1 Drawing Figure

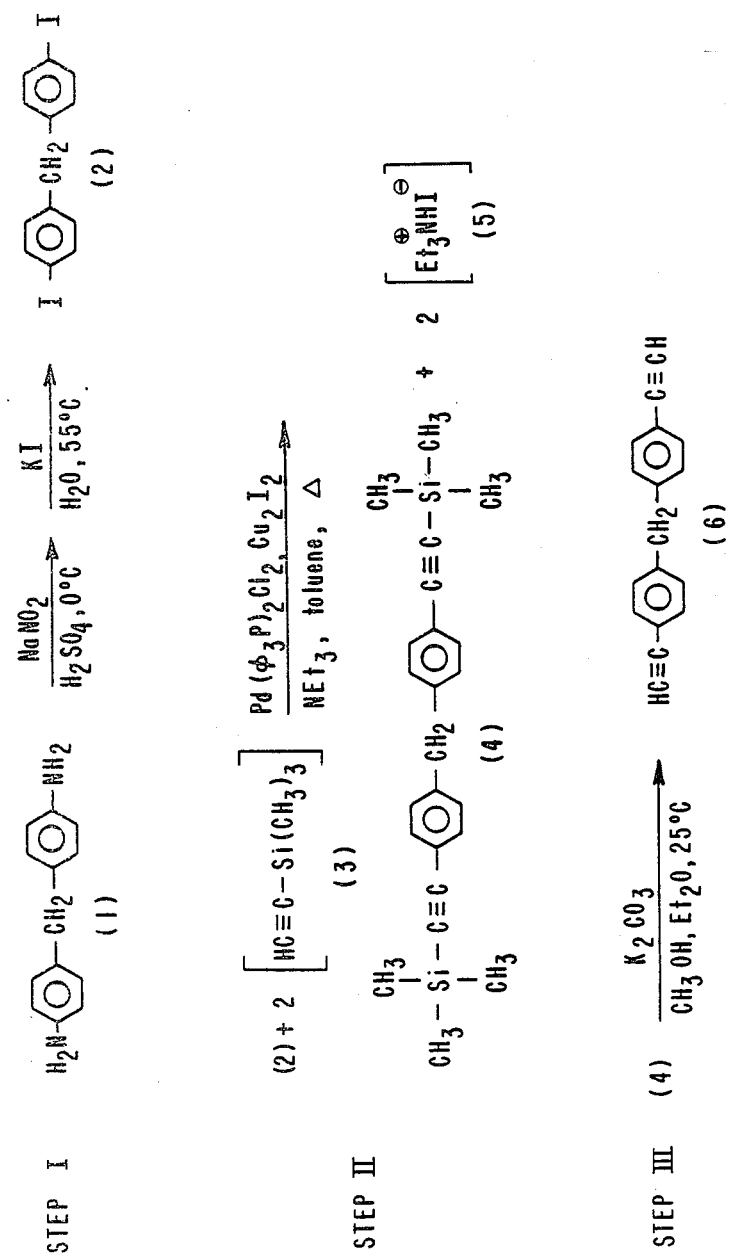

SYNTHESIS OF BIS(ETHYNYLPHENYL) COMPOUNDS

TECHNICAL FIELD

This invention relates, generally, to the synthesis of ethynylphenyl compounds and more particularly to the synthesis of 4,4'-diethynyldiphenylmethane.

CROSS REFERENCE TO RELATED APPLICATIONS

This application is related to U.S. application Ser. No. 197,300 filed Oct. 15, 1980 by applicant and another for "Ethynylated Aromatic Compounds and Process for Making Same". It differs from application Ser. No. 197,300 in that this application discloses a process for preparing bis(ethynylphenyl) compounds in contradistinction to the disclosure, in U.S. application Ser. No. 197,300, of ethynylated aromatic compounds having base sensitive substitutents. Both applications are commonly assigned to Hughes Aircraft Company of Culver City, Calif.

BACKGROUND OF THE INVENTION

1. Field of the Invention

Bis(ethynylphenyl) compounds, also known as ethynylated bis-aryl derivatives, are important intermediates in the synthesis of thermally stable resins for use in high-temperature structural composites, and high-char yielding structure matrices, such as carbon-carbon composites. These materials are used in the fabrication of reentry missile nose cones, leading edges, rocket nozzles, and other structural applications requiring high structural strength and high thermal stability. The invention disclosed below describes a simplified process for preparing these intermediates in high yields that may readily be adapted to large-scale synthesis operations.

2. Description of the Prior Art

Classical methods for the synthesis of terminal aryl acetylenes in general involve manipulation of preformed two-carbon side chains and include methods such as the Vilsmeier method, the halogenation dehydrohalogenation sequence of vinyl aromatics and aromatic ketones and the dehydrohalogenation of β, β-dihalo olefins. Methods that deviate from the classical approach have utilized the decomposition of preconstructed heterocycles. More recently, acetylenic substituents have been introduced onto aromatic nuclei by the Stephens-Castro coupling reaction. Since this reaction requires a stoichiometric quantity of an acetylenic copper reagent, prior preparation of such a reagent is needed, which consumes time, materials and energy. Also, the Stephens-Castro reaction requires the use of end-protecting groups such acetals, ketones, ketals, hydroxymethyl, tetrahydropyran-protected hydroxymethyl, dimethylcarbinol, or ethyl vinyl ether-protected carbinol. The removal of these groups often requires several steps and/or strongly alkaline media which tend to attack either the acetylenic linkage of the ethynyl group or any electron-withdrawing substituents on the aromatic nucleus. Therefore, there is a need for a simple process for preparing bis(ethynylphenyl) compounds in good yield that is suitble for large-scale synthesis operations. In particular, there is a need for a process for preparing 4,4'-diethynyldiphenylmethane in good yield.

SUMMARY OF THE INVENTION

In seeking to provide an improved process for the synthesis of 4,4'-diethynyldiphenylmethane in high yields that is suitable for large-scale synthesis operations, while avoiding the disadvantages of the prior art and at the same time retaining the advantages of the prior art, it has been discovered that bis(ethynylphenyl) compounds may be prepared in high yields by first providing a dihalogenated diphenyl compound, coupling the dihalogenated compound with ethynyltrimethylsilane in the presence of an organometallic catalyst to form a silylated ethynyl terminated diphenyl substituted compound and subsequently desilylating the compound to form the desired bis(ethynylphenyl) compound.

The process of this invention begins, for convenience, with the diazotization of a dianiline compound having the structure

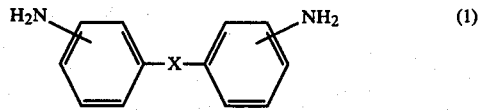  (1)

where X is a single bond, $CO$, $SO_2$, $NC_6H_5$, $S$, $Si(CH_3)_2$, $POCH_3$, $POC_6H_5$, $(CH_2)_n$, or $C(CF_nH_{3-n})_2$, where n is 0, 1, 2 or 3, to form an intermediate dihalodiphenyl compound. Alternatively, it may begin with the provision of the dihalodiphenyl compound. The diazotization of the above dianiline is accomplished by treating it with $NaNO_2$ and a selected inorganic halide in a strong acid, as is well-known. The dihalodiphenyl intermediate is then reacted with ethynyltrimethylsilane (in a coupling reaction) in an amine solvent in the presence of a catalytic mixture formed from an organometallic complex and a ligand, thereby forming a bis(trimethylsilyl)ethynylated derivative. The bis(trimethylsilyl)ethynyl derivative is then treated with a weak base in an ether-alcohol solvent to thereby form the desired diethynyl compound.

It is therefore one purpose of this invention to provide a generalized process for synthesizing bis(ethynylphenyl) compounds in high yields.

A further purpose of this invention is to provide an improved process for synthesizing 4,4'-diethynyldiphenylmethane in high yields.

A still further purpose of this invention is to provide intermediates for use in the synthesis of oligomers and resins suitable for use in the fabrication of high strength, high thermal stability compounds.

That I have accomplished these purposes, and others, will be apparent upon reference to the following drawing and detailed description of the invention.

BRIEF DESCRIPTION OF THE FIGURE

The FIGURE is a schematic of a reaction process for producing 4,4'-diethynyldiphenylmethane.

DETAILED DESCRIPTION OF THE INVENTION

It has been discovered that dihalogenated diphenyl compounds can be coupled with ethynyltrimethylsilane in the presence of an organometallic catalyst to produce a silylated ethynyldiphenyl compound that may be subsequently desilylated to quantitatively yield a bis(ethynylphenyl) compound. The process of this invention may begin with the provision of the dihalo diphenyl compound from commercial sources or it may begin with a diamino diphenyl (or dianiline) compound whose structure is:

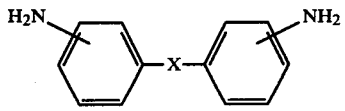

where $\underline{X}$ is a single bond, CO, SO$_2$, NC$_6$H$_5$, S, Si(CH$_3$)$_2$, POCH$_3$, POC$_6$H$_5$, (CH$_2$), or C(CF$_n$H$_{3-n}$)$_2$, where n is 0, 1, 2, or 3. These compounds are known in the art and some of them can be obtained from suppliers such as Aldrich Chemicals of Milwaukee, Wis., Eastman Chemical Co. of Rochester, N.Y., and Tridom Chemical Inc. of Hauppauge, N.Y.; others can be synthesized by available procedures that are known in the art. For practical applications, meta and/or para-substituted dianilines are selected. Ortho-substituted dianilines are not practical in that polymerization with ortho-substituted ethynyl groups is difficult.

The diaminophenyl compounds of (1) are diazotized to form aromatic halides whose structures are

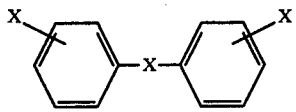

where $\underline{X}$ is I or Br and X is as defined above, by forming a slurry of the aminophenyl compound in a strong acid (in excess) with NaNO$_2$ (in a slight excess). As is well-known in the art, the temperature of the slurry is held below 5° C. for safety considerations. An inorganic halide such as KI, NaI or Cu$_2$Br$_2$ is subsequently added and the mixture is warmed to initiate the reaction. Acids such as HCl, H$_2$SO$_4$ and HBr are suitable. The strength of acid required is approximately inversely proportional to the strength of the basicity of the dianiline compound utilized.

Having obtained an aromatic halide of structure (2) in high purity, one then proceeds to couple the halide with ethynyltrimethylsilane (thereby introducing acetylenic moieties onto the molecule) by mixing the two compounds in deaerated toluene or benzene and any convenient amine solvent such as triethylamine, tripropylamine, or pyridine and warming the mixture in the presence of an organopalladium complex such as dichlorobis(triphenylphosphine)palladium[II], a ligand and an inorganic reducing agent to form a bis(trimethylsilylethynyl)diphenyl derivative. When a dichlorobis(-triphenyl-phosphine)palladium[II] is employed, it is necessary to add a reducing agent such as Cu$_2$I$_2$ to ensure quantitative yields. A catalytic mixture containing palladium acetate is also suitable for this coupling reaction. Stabilizing ligands such as triphenylphosphine, tris(o-(tolyl)phosphine, triphenylarsine, and triphenylstibine are suitable, although triphenylphosphine is most commonly used because of its availability and low cost. After workup and distillation, quantitative yields of the end-protected bis(trimethylsilylethynyl) diphenylderivative are formed for subsequent conversion to the bis(ethynylphenyl) derivative.

The final step of this process is accomplished by forming a solution of the end-protected diphenyl derivative in an anhydrous low boiling alcoholic solvent and subsequently adding a weak base, such as anhydrous potassium carbonate, with stirring under an inert atmosphere at room temperature. Short chain aliphatic alcohols such as methanol, ethanol, iso-propyl alcohol, and tert-butyl alcohol are suitable. However, in some instances, it may be necessary to form an alcohol-ether mixture to increase the solubility of the ethynylated derivative in the solvent.

Inasmuch as the removal of the end-protecting groups, or desilylation, is accomplished in the presence of a weak base in contrast to the prior art practice of utilizing a strong base, base-sensitive substituents on the molecule are tolerated.

A specific example of this process is shown below in connection with the FIGURE.

EXAMPLE

Preparation of 4,4'-Diiododiphenylmethane

In Step I, 4,4'-diaminodiphenylmethane [Compound (1)] was diazotized to form 4,4'-diiododiphenylmethane [Compound (2)] by forming a slurry of 17.0 g (85.9 mmoles) of 4,4'-diaminodiphenylmethane in 300 ml concentrated sulfuric acid and stirring at 25° C. until all solid particles dissolved. A dark brown solution was obtained and subsequently cooled to 0°–5° C. while a 30 ml aqueous solution of 17.0 g (0.239 mole) of sodium nitrite was added dropwise. Care was taken not to let the temperature of the mixture rise above 5° C. After the addition of sodium nitrite was completed, the slurry was stirred for 30 minutes at 5° C. and then slowly poured into an aqueous solution of 100 g of potassium iodide in 2 liters of water preheated to 55° C. The resulting mixture was stirred for 1 hour at 55° C., cooled to 25° C., mixed with 1 liter of dichloromethane, neutralized with the addition of 50% aqueous sodium hydroxide, and then decolorized with saturated aqueous sodium bisulfite solution. A brown organic phase was obtained which was separated and washed with 500 ml each of 10% aqueous hydrochloric acid, distilled water, saturated aqueous sodium bicarbonate, and then water. After drying over magnesium sulfate and concentrating on a rotary vacuum evaporator, the residual crude oil was purified by column chromatography through silica gel using hexane as eluant to yield a white crystalline solid. The white crystalline solid was identified as 4,4'-diiododiphenylmethane: 15.0 g (35.7 mmoles, 41.6%); mp 85°–86° C.; IR (KBr) 2950 (weak, sharp CH), 1490, 1400 (strong, sharp, C≡C), 1020, 810, 780 cm$^{-1}$ (strong, sharp); NMR (CDCl$_3$) δ3.83 (s, 2H, CH$_2$), 6.87 and 7.60 ppm (q, 8H, J$_{AB}$=8.0 Hz, aromatic).

Preparation of Bis(4-trimethylsilylethynylphenyl)methane

In Step II, 4,4'-diiododiphenylmethane [Compound (2)] was then coupled with ethynyltrimethylsilane [Compound (3)] to form an end-protected bis(4 trimethylsilylethynylphenyl) methane [Compound (4)] by forming a solution comprising 8.40 g (20.0 mmoles) of 4,4'-diiododiphenylmethane and 2.50 g (25.5 mmoles) of ethynyltrimethylsilane in 150 ml of 2:1 triethylamine toluene deaerated with argon. This solution was subsequently treated with a catalyst mixture comprising 50 mg of dichlorobis(triphenylphosphine)palladium[II], 150 mg of triphenylphosphine and 50 mg of copper[I] iodide. The yellow solution thus obtained was stirred and warmed to 80°–90° C. over 1 hour and kept in this temperature range for 4 hours. A copious white precipitate was formed which was filtered off after cooling to 25° C. and diluting with 150 ml of ether. The yield of triethylamine hydroiodide [Compound (5)] was quantitative. The filtrate was concentrated to a thick oil, dissolved in 200 ml of ether and washed with 200 ml each of 10% aqueous hydrochloric acid, water, saturated aqueous sodium bicarbonate, and water again. The ethereal phase was dried over magnesium sulfate and concentrated to an oil which crystallized on standing. The solid was taken up in 100 ml of 1:1 hexane/dichloromethane and filtered through a bed of silica gel. The filtrate was evaporated down to half of the original volume and cooled at −78° C. to precipitate 7.20 g (20.0 mmoles; 100%) of a crystalline solid. Recrystallization from hexane yielded pure, lustrous crystals in 81% recovery: mp 110°–111° C.; IR (KBr) 2970 (strong, sharp, SiCH$_3$), 2160 (strong, sharp, C≡C), 1505 (strong, sharp, C=C), 1250 (strong, sharp, SiCH$_3$) and 840 cm (very strong, broad, Si—C bending); NMR (CDCl$_3$) δ0.28 (s, 18H, SiC$\underline{H}_3$), 3.92 (s, 2H, C$\underline{H}_2$), 7.37 and 7.40 ppm (q, 8H, J$_{AB}$=8.0 Hz, aromatic).

Analysis: for C$_{23}$H$_{28}$Si$_2$(360.6): Calculated: C,75.49; H,7.83; Si,15.58. Found: C,76.28; H,7.84; Si,15.84.

Preparation of 4,4′-Diethynyldiphenylmethane

In Step III, a suspension of 1.00 g (2.78 mmoles) of bis(4-trimethylsilylethynylphenyl) methane [Compound (4)] in 50 ml anhydrous deaerated methanol was treated with enough anhydrous ethyl ether to dissolve all solid particles at 25° C. Anhydrous potassium carbonate (300 mg) was added and the mixture was stirred at 25° C. under argon for 16 hours. The solvent was removed and the solid residue was dissolved in 50 ml dichloromethane, treated with 5 g of silica gel and evaporated to dryness. The powder was placed on top of a 40-cm (I.D. 30 mm) column of silica gel (EM Labs, 70–230 mesh) and the column was developed with passage of hexane. A crystalline white solid [Compound (6)] was recovered from the the eluate: 0.60 gm (2.78 mmoles, 100%); mp 63°–64° C. After drying at 56° C./0.01 mm Hg inside an Abderhalden apparatus for 2 hours, the mp increased to 65.5°–66.5° C. IR (KBr) 3280 (very strong, sharp, —C≡CH), 2100 (weak, sharp, —C≡C—), and 1500 cm$^{-1}$(medium, sharp, C=C); MS (70 eV) m/e 216 (molecular ion); NMR (CDCl$_3$) δ3.03 (s,2H,C≡C—$\underline{H}$), 3.95(s,2H,C$\underline{H}_2$), 7.10 and 7.43 ppm (q,8H, J$_{AB}$=8.0 Hz, aromatic).

Analysis: for C$_{17}$H$_{12}$(216.3): Calculated: C,94.41; H,5.59. Found: C,94.34; H,5.70.

The example shown above is intended as an illustration only and is not to be construed as a limitation. This invention encompasses variations about the general teachings which are within the skills of those who practice in this art such as the utilization of other organometallic complexes as catalyst, temperature optimizations, and the selection of other suitable solvents.

Bis(ethynylphenyl) compounds prepared in accordance with this invention may be used to form copolymers as taught in U.S. Pat. No. 4,098,767 and carbon-carbon compositions as described and claimed in U.S. Pat. No. 4,284,834.

What is claimed is:

1. A process for preparing bis(ethynylphenyl) compounds in high yields comprising the steps of diazotizing a dianiline whose structure is

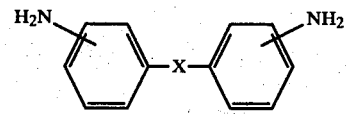

where X is a single bond, CO, SO$_2$, NC$_6$H$_5$, S, Si(CH$_3$)$_2$, POCH$_3$, POC$_6$H$_5$, (CH$_2$)$_n$, or C(CF$_n$H$_{3-n}$)$_2$ where n is 0, 1, 2 or 3 to form a dihalogenated diphenyl compound;

coupling said diphenyl compound with ethynyltrimethylsilane in the presence of an organopalladium complex and a ligand to yield an end-protected diphenyl compound having acetylenic moieties thereon; and subsequently removing said end-protecting groups from said diphenyl compound by treating said compound with a weak base in an inert atmosphere.

2. The process of claim 1 wherein an inorganic halide selected from the group consisting of NaI, KI and Cu$_2$Br$_2$, is employed to form said dihalogenated diphenyl compound, said palladium complex is dichlorobis(triphenylphosphine)palladium[II] or palladium acetate, and said ligand is selected from the group consisting of triphenylphosphine, tris(o-tolyl)phosphine, triphenylarsine, and triphenylstibine.

3. The process of claim 2 wherein said acid is H$_2$SO$_4$, said halide is KI, said palladium complex is dichlorobis(triphenylphosphine)palladium[II], said ligand is triphenylphosphine and said weak base is K$_2$CO$_3$.

4. An improved process for synthesizing bis(ethynylphenyl) compounds having the structure

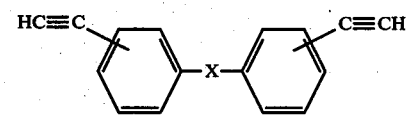

where X is a single bond, CO, SO$_2$, NC$_6$H$_5$, S, Si(CH$_3$)$_2$, POCH$_3$, POC$_6$H$_5$, (CH$_2$)$_n$ or C(CF$_n$H$_{3-n}$)$_2$, where n is 0, 1, 2, or 3, comprising the steps of:

diazotizing a dianiline whose structure is

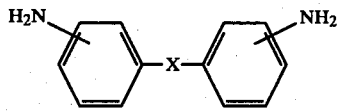

where X is as defined above, by treating said dianiline with NaNO$_2$, an organic halide selected from the group consisting of KI, NaI and Cu$_2$Br$_2$ and a strong acid selected from the group consisting of HCl, H$_2$SO$_4$ and HBr to form a dihalo diphenyl intermediate compound;

forming a reaction mixture of said dihalo compound with ethynyltrimethylsilane in triethylamine-toluene;

warming said reaction mixture in the presence of a catalytic mixture formed from dichlorobis(triphenylphosphine)palladium[II], triphenylphosphine and copper iodide, thereby forming a bis(trimethylsilyl)ethynyl derivative; and desilylating said ethynyl derivative by treating it with a weak base in an ether alcohol solvent, thereby forming the desired diethynyldiphenyl product in high yields.

5. The process of claim 4 wherein X is CH₂ and said weak base K₂CO₃.

6. A process for preparing 4,4'-diethynyldiphenylmethane in high yield comprising the steps of:
   forming a slurry of 4,4'-diaminodiphenylmethane in concentrated sulfuric acid, adding NaNO₂ to said slurry and mixing said slurry with an aqueous solution of an inorganic halide to form a dihalogenated diphenylmethane;
   coupling said dihalogenated diphenylmethane with ethynyltrimethylsilane by warming and stirring a mixture of said methane and said silane in the presence of an organopalladium catalytic complex, a ligand and deareated triethylamine and toluene to provide an end-protected diphenylmethane compound having acetylenic moieties as substituents; and
   subsequently treating said end-protected compound with a weak base in an alcohol-ether solvent to remove said end-protecting groups, thereby yielding 4,4'-diethynyldiphenylmethane.

7. The process of claim 6 wherein said inorganic halide is KI, said catalytic complex is formed from dichlorobis(triphenylphosphine)palladium[II] and Cu₂I₂, said ligand is triphenylphosphine, and said base is K₂CO₃.

8. An improved process for synthesizing bis(ethynylphenyl) compounds whose structures are

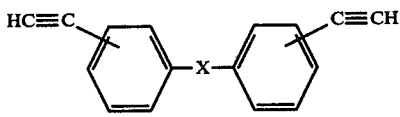

where X is a single bond, CO, SO₂, NC₆H₅, S, Si(CH₃)₂, POCH₃, POC₆H₅, (CH₂)ₙ or C(CFₙH₃₋ₙ)₂ where is 0, 1, 2 or 3 comprising the steps of:
   coupling ethynyltrimethylsilane with a dihalo diphenyl compound whose structure is

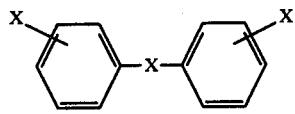

where X̲ is I or Br and X is as defined above to provide an end-protected diphenyl compound having acetylenic moieties thereon; and
   subsequently treating said end-protected diphenyl compound with a weak base in an alcoholic solvent.

9. The process of claim 8 wherein ethynyltrimethylsilane is reacted with said diphenyl compound in the presence of an organopalladium catalyst, a ligand, and an amine solvent.

10. The process of claim 9 wherein said organopalladium catalyst is dichlorobis(triphenylphosphine)palladium[II].

11. The process of claim 10 wherein said diphenyl compound is 4,4'-diiododiphenylmethane.

* * * * *